United States Patent
Amano et al.

(10) Patent No.: US 6,190,374 B1
(45) Date of Patent: *Feb. 20, 2001

(54) APPARATUS FOR OPERATING UPON A CORNEA

(75) Inventors: Masanori Amano, Hazu-gun; Hirokatsu Makino, Toyohashi, both of (JP)

(73) Assignee: Nidek Co., Ltd. (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/978,029

(22) Filed: Nov. 25, 1997

(30) Foreign Application Priority Data

Nov. 29, 1996 (JP) ................................... 8-334592

(51) Int. Cl.$^7$ ........................................ A61N 5/06
(52) U.S. Cl. ................... 606/5; 606/4; 606/11; 606/12
(58) Field of Search ................. 606/4, 5, 6, 10, 606/11, 12

(56) References Cited

U.S. PATENT DOCUMENTS

| | | | |
|---|---|---|---|
| 4,911,711 | * 3/1990 | Telfair et al. | 606/5 |
| 5,163,934 | * 11/1992 | Munnerlyn | 606/5 |
| 5,219,344 | * 6/1993 | Yoder, Jr. | 606/5 |
| 5,314,422 | 5/1994 | Nizzola | 606/5 |
| 5,395,356 | * 3/1995 | King et al. | 606/4 |
| 5,411,501 | * 5/1995 | Kloptek | 606/4 |
| 5,445,633 | * 8/1995 | Nakamura et al. | 606/5 |
| 5,470,329 | * 11/1995 | Sumiya | 606/4 |
| 5,507,799 | 4/1996 | Sumiya | 606/5 |
| 5,549,599 | * 8/1996 | Sumiya | 606/10 |
| 5,556,395 | * 9/1996 | Shimmick et al. | 606/4 |
| 5,562,656 | 10/1996 | Sumiya | 606/4 |
| 5,569,238 | * 10/1996 | Shei et al. | 606/4 |
| 5,620,437 | * 4/1997 | Sumiya | 606/5 |
| 5,624,436 | * 4/1997 | Nakamura et al. | 606/12 |
| 5,637,109 | * 6/1997 | Sumiya | 606/5 |
| 5,642,287 | * 6/1997 | Sotiropoulos et al. | 606/5 |
| 5,827,264 | * 10/1998 | Hohla | 606/5 |

FOREIGN PATENT DOCUMENTS

| | | |
|---|---|---|
| 6-327710 | 11/1994 | (JP) . |
| 8-066420 | 3/1996 | (JP) . |
| 9-24060 | 1/1997 | (JP) . |

* cited by examiner

Primary Examiner—Linda C. M. Dvorak
Assistant Examiner—David M. Ruddy
(74) Attorney, Agent, or Firm—Finnegan, Henderson, Farabow, Garrett & Dunner, L.L.P.

(57) ABSTRACT

An apparatus for operating upon a cornea for delivering a laser beam having wavelength in an ultraviolet range emitted from a laser light source to the cornea, and for correcting ametropia by ablating the cornea with the laser beam, the apparatus comprises a correcting-hypermetropia optical system having a first aperture to restrict an ablation area, for correcting hypermetropia by changing a passing area for the laser beam, input device for inputting information necessary for defining a corneal shape after ablation, controlling device for defining an ablation shape based on the information inputted by the input device, and for driving the laser light source and the correcting-hypermetropia optical system, and a second aperture located by decentering for the center of the cornea, for transmitting the laser beam within an area of a near-point portion, whereby correction of presbyopia may be performed so that the cornea has double focal points by driving the laser light source and the correcting-hypermetropia optical system under condition that the second aperture is located at a predetermined position.

15 Claims, 11 Drawing Sheets

FIG. 5

| Shifted position | a | b | c | d | e | f | g | h | i |
|---|---|---|---|---|---|---|---|---|---|
| Shifting distance from the oprical axis L (mm) | 1.4 | 2.8 | 4.2 | 5.6 | 7.0 | 8.4 | 9.8 | 11.2 | 12.6 |

FIG. 10

| Shifted position | a | b | c | d | e | f | g | h | i |
|---|---|---|---|---|---|---|---|---|---|
| Ratio of the laser beam irradiation time | 1 | 4 | 9 | 16 | 25 | 36 | 49 | 64 | 81 |

FIG. 11

| Ablation condition | Laser irradiation time (sec) | | | | | | | | | Total |
|---|---|---|---|---|---|---|---|---|---|---|
| | a | b | c | d | e | f | g | h | i | |
| A | 1 | 4 | 9 | 16 | 25 | 36 | 49 | 64 | 81 | 285 |
| B | 2 | 8 | 18 | 32 | 50 | 72 | 98 | 128 | 168 | 570 |
| C | 0.5 | 2 | 4.5 | 8 | 12.5 | 18 | 24.5 | 32 | 40.5 | 142.5 |
| D | 1.5 | 6 | 13.5 | 24 | 37.5 | 54 | 73.5 | 96 | 121.5 | 427.5 |

Shifted position: c

Shifted position: d

Shifted position: e

PRIOR ART

APPARATUS FOR OPERATING UPON A CORNEA

BACKGROUND OF THE INVENTION

1. Field of the Invention

The present invention relates to an apparatus for operating upon a cornea for correcting ametropia of the cornea by using a laser beam, and more particularly to the apparatus suitable for not only the correction of hypermetropia or myopia but also the correction of presbyopia.

2. Description of Related Art

An apparatus for operating upon a cornea is well-known that a corneal surface is ablated by using a laser beam, and ametropia of an eye-ball is corrected by changing a corneal curvature.

There are some types of ametropia of an eye; myopia, astigmatism, hypermetropia, also presbyopia in which someone cannot recognize a near point as they become older. An apparatus for the correction of presbyopia has been well-known as shown in the specification of U.S. Pat. No. 5,314,422. In this apparatus, as shown in FIG. 16, two flat plates 101 and 102 are slidable in opposite directions respectively so as to open an aperture in a shape of a crescent, thereby a part of a cornea is irradiated with a laser beam through the aperture. As a result of this, the cornea is corrected so as to have double focal points like presbyopia glasses having additional lenses. Upon the operation, a frame 100 for supporting to allow the two plates to slide is mounted and fixed on the eye.

However, the above-mentioned apparatus has some demerits as follows. Apart from the body of the apparatus for operating upon the cornea which the laser beam is emitted, this apparatus also has a special mask for use in the correction of presbyopia. Since frame 100 should be mounted on the eye for positioning, it may be difficult to achieve such an accurate positioning so as to adjust within an expected ablation area.

Also, apart from the positioning of the laser beam, since the close-open operation for the two plates 101 and 102 is controlled, it is difficult to make the size of the aperture and the position of the beam be involved. Therefore, it is important to give attention to the beam irradiation for completely covering the aperture.

Further, because the correction degree is controlled by the close-open control of the aperture, it is difficult to adjust the amount of laser-beam irradiation in combination with the close-open operation of the aperture.

In addition, since the mask is arranged for covering the surface of the eye-ball, it results in another problem that an observation of the eye may be difficult during the laser irradiation.

SUMMARY OF THE INVENTION

An object of the invention is to overcome problems described above and to provide an apparatus for operating upon a cornea, which is capable of achieving the correction of presbyopia easily without any additional apparatus for presbyopia.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an apparatus for operating upon a cornea for delivering a laser beam having wavelength in an ultraviolet range emitted from a laser light source to the cornea, and for correcting ametropia by ablating the cornea with the laser beam, the apparatus comprises a correcting-hypermetropia optical system having a first aperture to restrict an ablation area, for correcting hypermetropia by changing a passing area for the laser beam, input means for inputting information necessary for defining a corneal shape after ablation, controlling means for defining an ablation shape based on the information inputted by the input means, and for driving the laser light source and the correcting-hypermetropia optical system, and a second aperture located by decentering for the center of the cornea, for transmitting the laser beam within an area of a near-point portion, whereby correction of presbyopia may be performed so that the cornea has double focal points by driving the laser light source and the correcting-hypermetropia optical system under condition that the second aperture is located at a predetermined position.

In another aspect of the present invention, an apparatus for operating upon a cornea for delivering a laser beam having wavelength in an ultraviolet range emitted from a laser light source to the cornea, and for correcting ametropia by ablating the cornea with the laser beam, the apparatus comprises a correcting-myopia optical system having an variable aperture at a aperture diameter, for correcting myopia by changing a passing area for the laser beam, input means for inputting information necessary for defining a corneal shape after ablation, controlling means for defining an ablation shape based on the information inputted by the input means, and for driving the laser light source and the correcting-myopia optical system, and intercepting means for intercepting the laser beam within an area of a near-point portion, whereby correction of presbyopia may be performed so that the cornea has double focal points by driving the laser light source and the correcting-myopia optical system under condition that the intercepting means is located at a predetermined position.

Also, in another aspect of the present invention, an apparatus for operating upon a cornea comprises a laser light source for emitting a laser beam having a beam intensity of Gaussian distribution, an ablation optical system for correcting ametropia of cornea by a method that an eye to be operated is irradiated with the laser beam emitted from the laser light source, a circular aperture located in the ablation optical system, for restricting an area which is ablated by the laser beam, beam moving means for moving the laser beam passed through the circular aperture in a direction of Gaussian distribution, beam rotating means for rotating a moving direction of the laser beam which is moved by the beam moving means, information input means for inputting information about the ablation area, controlling means for controlling one ablation for correcting hypermetropia with making the circular aperture shift based on the information inputted by the information input means, or for controlling other ablation for correcting myopia with partially intercepting the ablation area of the laser beam, whereby the cornea is ablated so as to have double focal points, and the correction of presbyopia may be performed.

As described above, and in accordance with the present invention, the apparatus enables the correction of presbyopia within the expected ablation area without using any additional apparatus for presbyopia apart from the body of the apparatus for operation on for a cornea.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention.

In the drawings,

FIG. 5 is a view showing shifting distance of the center of beam from an optical axis L at shifted positions a–i in the present invention;

FIG. 10 is a sample showing a combination of laser irradiation time at each shifted position for ablating to be a convex-lens shape in the present invention;

FIG. 11 is a view showing a condition setting of various ablations by changing the whole laser irradiation time without any change of a ratio of the irradiation time at each shifted position in the present invention;

DETAILED DESCRIPTION OF THE PREFERRED EMBODIMENTS

Figure 1:
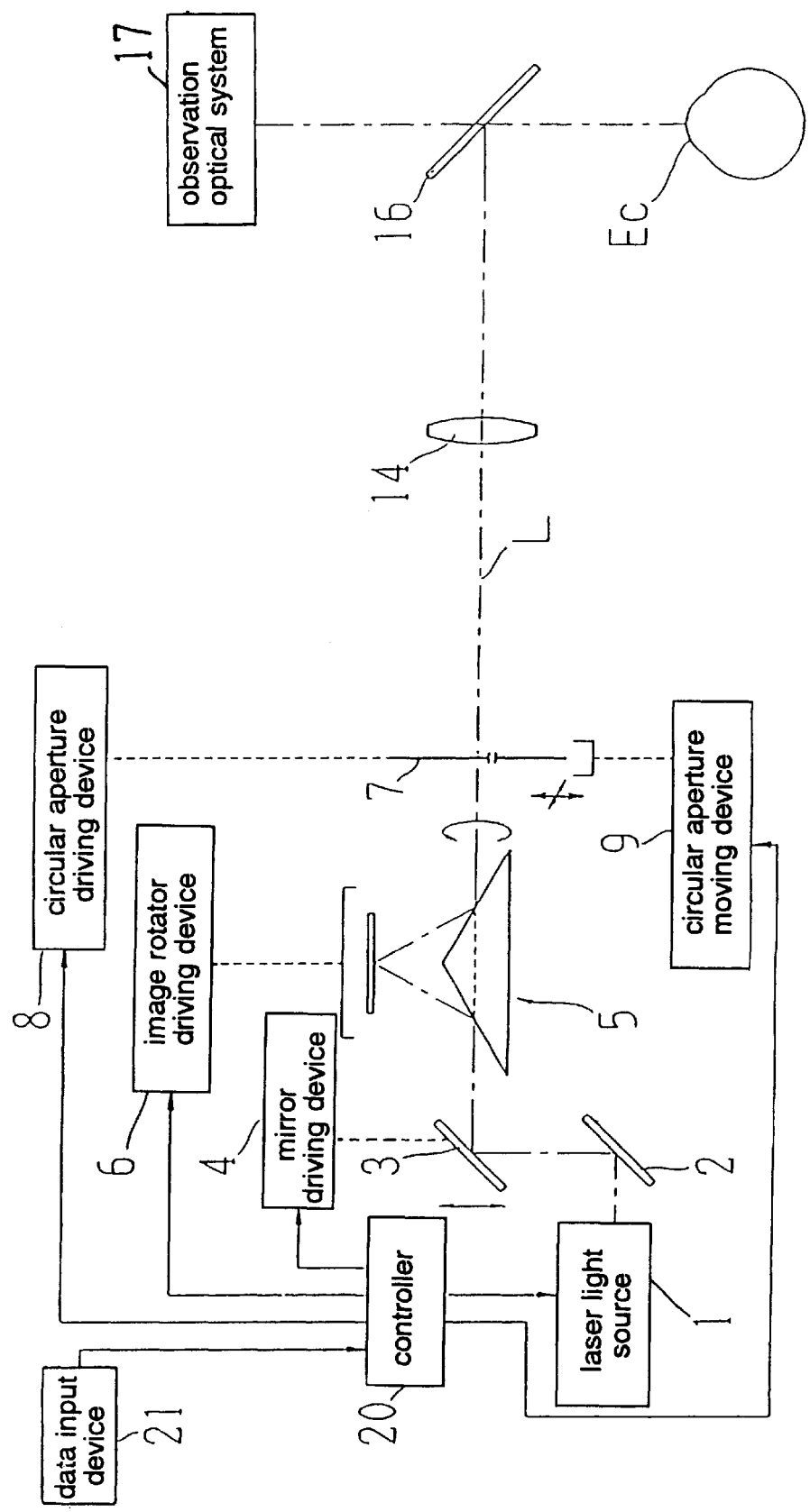
FIG. 1 is a view showing an outline arrangement of an optical system and a control system of an apparatus for operating upon a cornea related to the preferred embodiment of the present invention.

A detailed description of the present invention is provided below with reference to the accompanying drawing. FIG. 1 is a view showing an outline arrangement of an optical system and a control system of the apparatus of the preferred embodiment.

Figure 2:
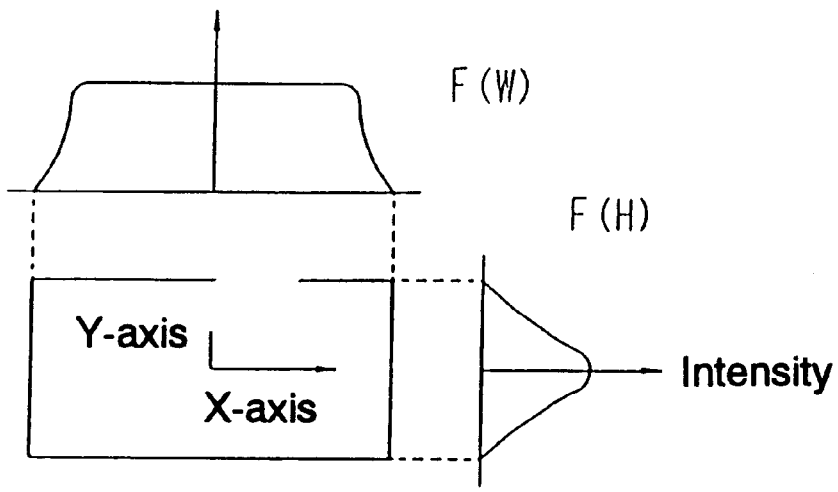
FIG. 2 is a view showing a typical shape of an excimer laser beam emitted from a laser light source for use in the optical system as shown in FIG. 1.

Numeral 1 is a laser light source, and an excimer laser beam having a wavelength of 193 nm is used in the preferred embodiment. It is desirable that the laser beam having the wavelength under 200 nm may be used. The excimer laser beam emitted from the laser light source 1 is a pulse wave, and as shown in FIG. 2, its typical pulse shape has intensity distributions; a top-hat distribution F(W) in a horizontal direction (X-axis direction), and a Gaussian distribution F(H) in a vertical direction (Y-axis direction).

Elements 2 and 3 are plane mirrors, so that the laser beam emitted from the laser light source 1 in the horizontal direction is deflected at 90 degree upward by the plane mirror 2, and then it is again deflected by the plane mirror 3 in the horizontal direction. The plane mirror 3 is movable in the vertical direction (an arrow direction) by a mirror driving device 4, thereby the laser beam emitted from the laser light source 1 is moved in parallel in a direction of the Gaussian distribution and the laser beam is shifted from an optical axis L of a light delivery optical system so as to ablate an object uniformly. The details of this point are provided in Japanese Laid Open No. 4-242644 (the title of invention "Ablation apparatus for ablating object by laser beam"), corresponding to U.S. Pat. No. 5,507,799 as a reference.

An image rotator 5 is rotated and driven at the center of the optical axis L by an image rotator driving device 6, so that the laser beam is rotated about the optical axis L.

Figure 3:
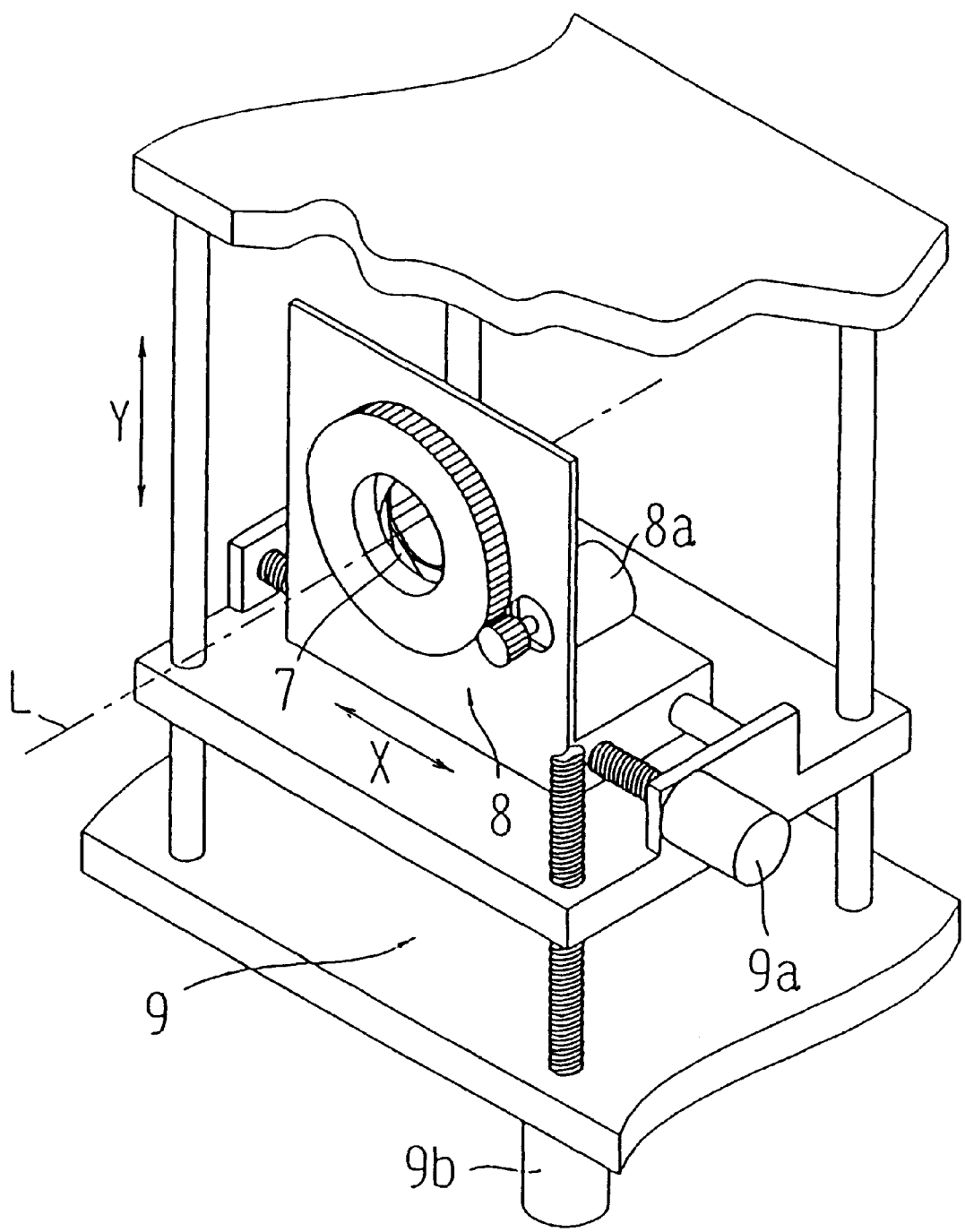
FIG. 3 is a view showing a moving device of a circular aperture for use in the optical system as shown in FIG. 1.
Figure 6A:
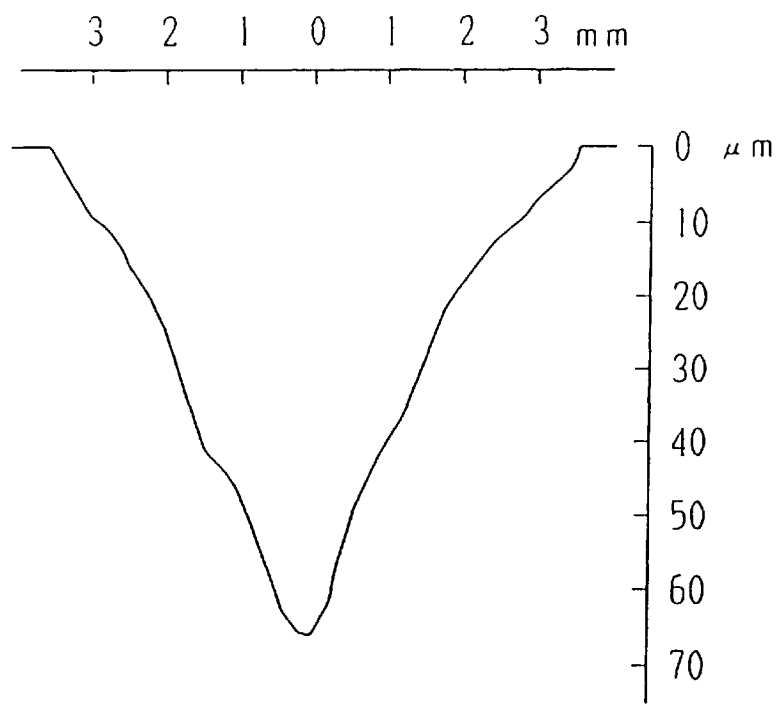
FIGS. 6A and 6B are views showing ablation sections when the laser is irradiated for a constant period (30 sec) at the shifted positions a and b as shown in FIG. 5.
Figure 6B:
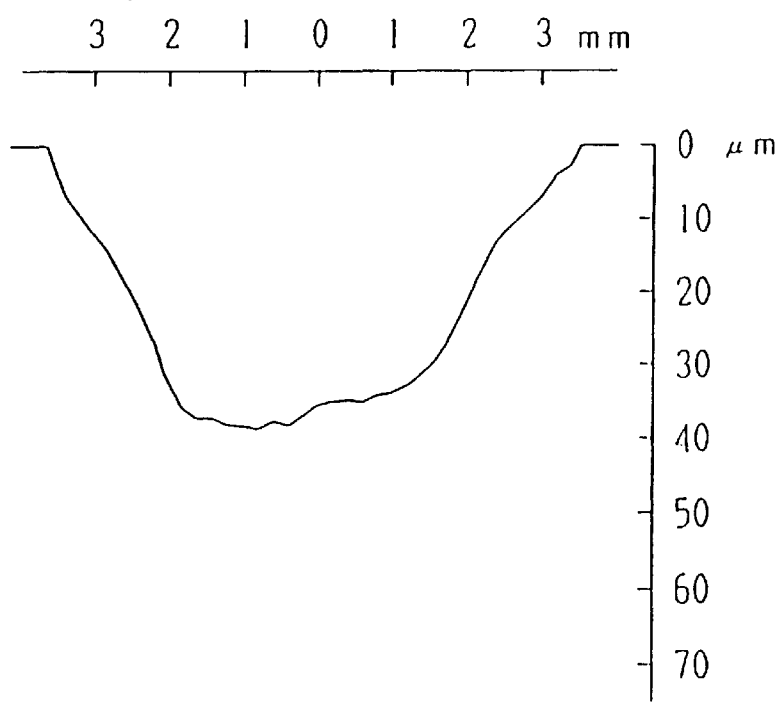
Figure 7C:
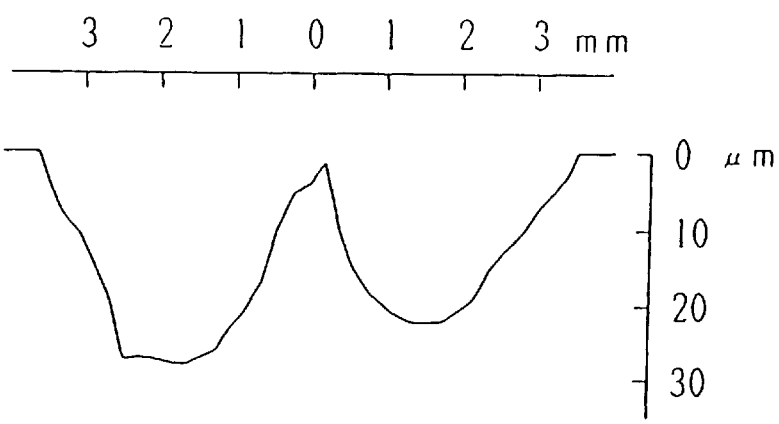
FIGS. 7C–7E are views showing ablation sections when the laser is irradiated for the constant period (30 sec) at the shifted positions c, d and e as shown in FIG. 5.
Figure 7D:
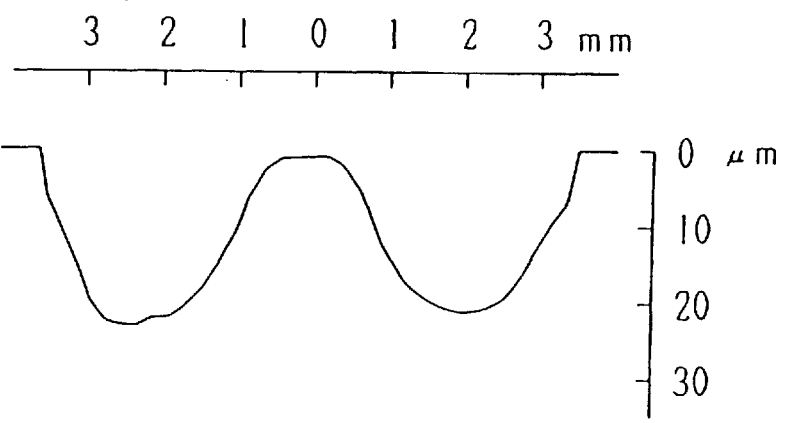
Figure 7E:
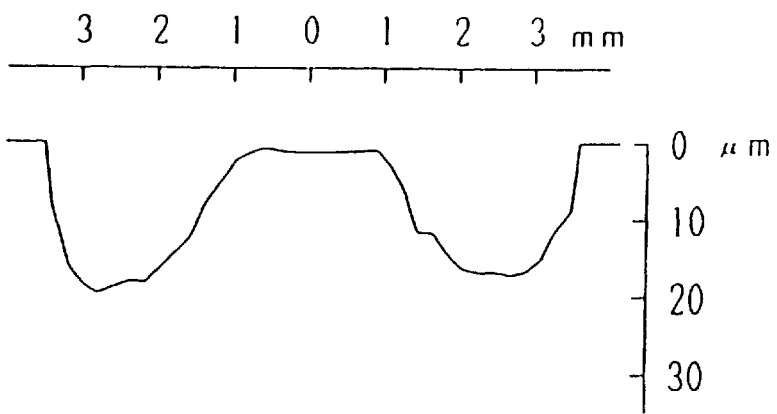
Figure 8F:
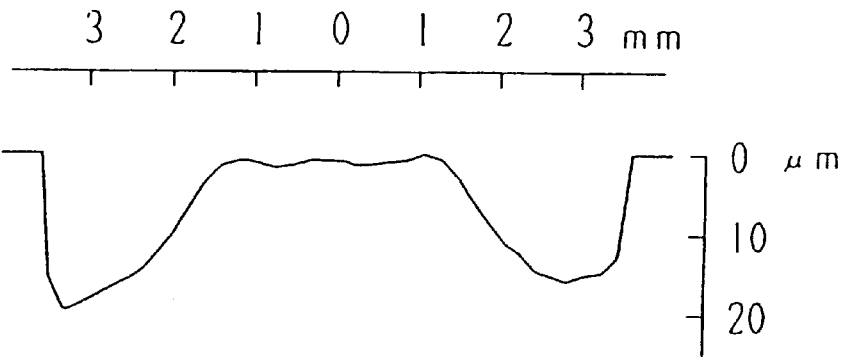
FIGS. 8F–8H are views showing ablation sections when the laser is irradiated for the constant period (30 sec) at the shifted positions f, g and h as shown in FIG. 5.
Figure 8G:
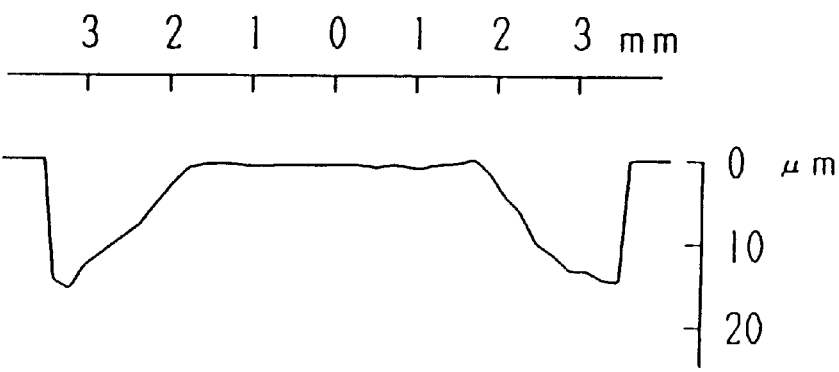
Figure 8H:
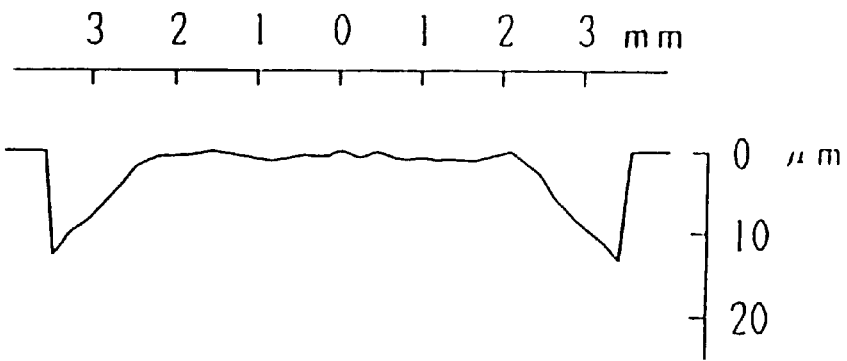
Figure 9:
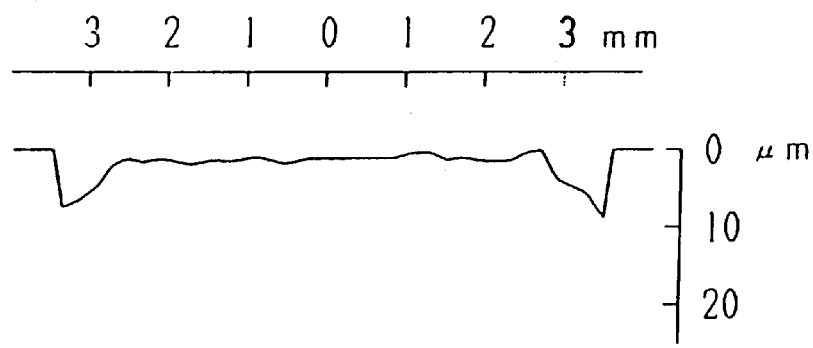
FIG. 9 is a view showing an ablation section when the laser is irradiated for the constant period (30 sec) at the shifted position i as shown in FIG. 5.

A variable circular aperture 7 is for restricting an ablation area to be a circular shape. The aperture diameter of the circular aperture 7 is variable by rotations of a motor 8a in the aperture driving device 8. Also, the circular aperture 7 is moved by motors 9a and 9b in a moving device 9 in a planar direction (X-direction, Y-direction) which is perpendicular to the optical axis L (as shown in FIG. 3).

Element 14 is a projection lens for projecting the circular aperture 7 onto a cornea Ec of a patient's eye. A dichroic mirror 16 has a characteristic of reflecting the excimer laser beam of 193 nm and of transmitting visible light.

Then, the laser beam passed through the projection lens 14 is reflected by the dichroic mirror 16 and is bent at 90 degrees so as to be delivered toward the cornea Ec. Further, the circular aperture 7 may be arranged between the cornea Ec and the dichroic mirror 16 so as to restrict the ablation area.

Numeral 17 is a observation optical system having binocular operation microscopes. The right and left observation optical systems are arranged so as to put the dichroic mirror 16 between them. Any other binocular observation optical systems which are on the open market may be available. Since the structural body is not related to the present invention, the detailed description will be omitted herein.

The patient's eye is aligned beforehand so as to achieve a predetermined positional relation with the apparatus for the operation. By a means that the patient fixes a fixation light (not illustrated) with the eye, the alignment condition may be maintained. In the alignment process, a slit image is projected onto the patient's eye at least from two directions by putting into the optical axis of the observation optical system, so that the alignment is performed based on the positional relation of the slit image. The detailed description is quoted from Japanese Laid Open No. 6-47001, corresponding to U.S. Pat. No. 5,562,656 by the applicant of the present invention.

A controller 20 is for controlling the whole of the apparatus, and a data input device 21 is for inputting the data related to the refractive power of the patient's eye or the like. The controller 20 controls each drive of devices based on the input information of corneal shapes before operation and after operation or the like inputted by the data input device 21.

The operation method of the above-mentioned apparatus will be explained in the above-mentioned apparatus. Firstly, the correction of myopia and the correction of hypermetropia will be described herein. The cornea of the patient's eye is fixed at a predetermined position opposite to the apparatus. The ablation area or its shape is determined by following programs stored into the controller 20 based on the data of the refractive power or the like which are inputted beforehand by the data input device 21.

In case of the correction of myopia, the center of the circular aperture 7 is conformed with the optical axis L. The laser beam is restricted by the aperture 7, so that the laser beam is moved in the direction of the Gaussian distribution by moving the mirror 3 in sequence. Then, every movement that the laser beam finishes moving on a surface from one edge to other edge of the circular aperture 7, the moving direction of the laser beam is rotated by the image rotator 5 so as to ablate to be an uniform circular shape. This process is performed by changing the size of the aperture diameters of the circular aperture 7 in sequence. As a result of this, the center part of the cornea is ablated deeply, and the peripheral part is ablated shallowly, thereby the correction of myopia can be achieved (refers to Japanese Laid Open No. 6-114083 corresponding to U.S. Pat. No. 5,637,109).

Next, the correction of hypermetropia will be explained herein. The method of correcting hypermetropia will be described by using a plate material, PMMA (polymethylmethacrylate) instead of a cornea.

Figure 4:
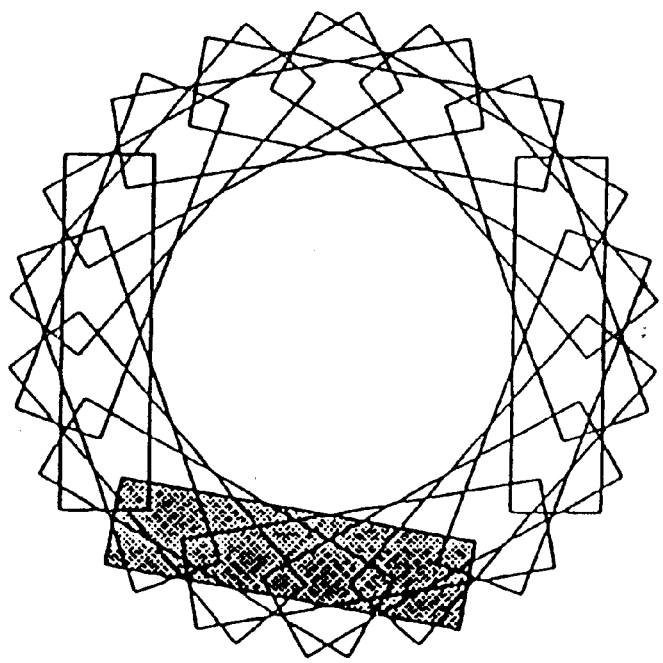
FIG. 4 is a view showing a looped ablation shape upon the correction of hypermetropia in the present invention.

The center of the circular aperture 7 is conformed with the optical axis L, and the aperture diameter is fixed in accordance with the ablation area. The laser beam is shifted opposite to the optical axis L by moving the mirror 3 so as to lap over the ablation by rotating the image rotator 5. The ablated shape may be formed into a looped shape by appropriately selecting a combination of rotation frequencies of the image rotator 5 and multiple frequencies of the laser pulse. For instance, assuming that the rotation frequencies of the image rotator 5 are 10 Hz, and the multiple frequencies of the laser pulse are 23 Hz, such a looped ablation shape may be formed as shown in FIG. 4.

In order to achieve such a looped ablation, the beam center may be shifted at a certain interval (1.4 mm) opposite to the optical axis L by the movement of the mirror 3 as shown FIG. 5. FIGS. 6–9 are views showing ablation sections when the laser is irradiated for a certain period (30 sec) at shifted positions a–i.

When the laser irradiation time is equal, the center parts are ablated deeply when the shifting distance of the beam center is small. On the other hand, the periphery parts are ablated outward for preventing the center part from being ablated, when the shifting distance of the beam center is large. Then, since there are much beam eclipse caused by the circular aperture 7, the depth of periphery are getting shallower in sequence.

Figure 12:
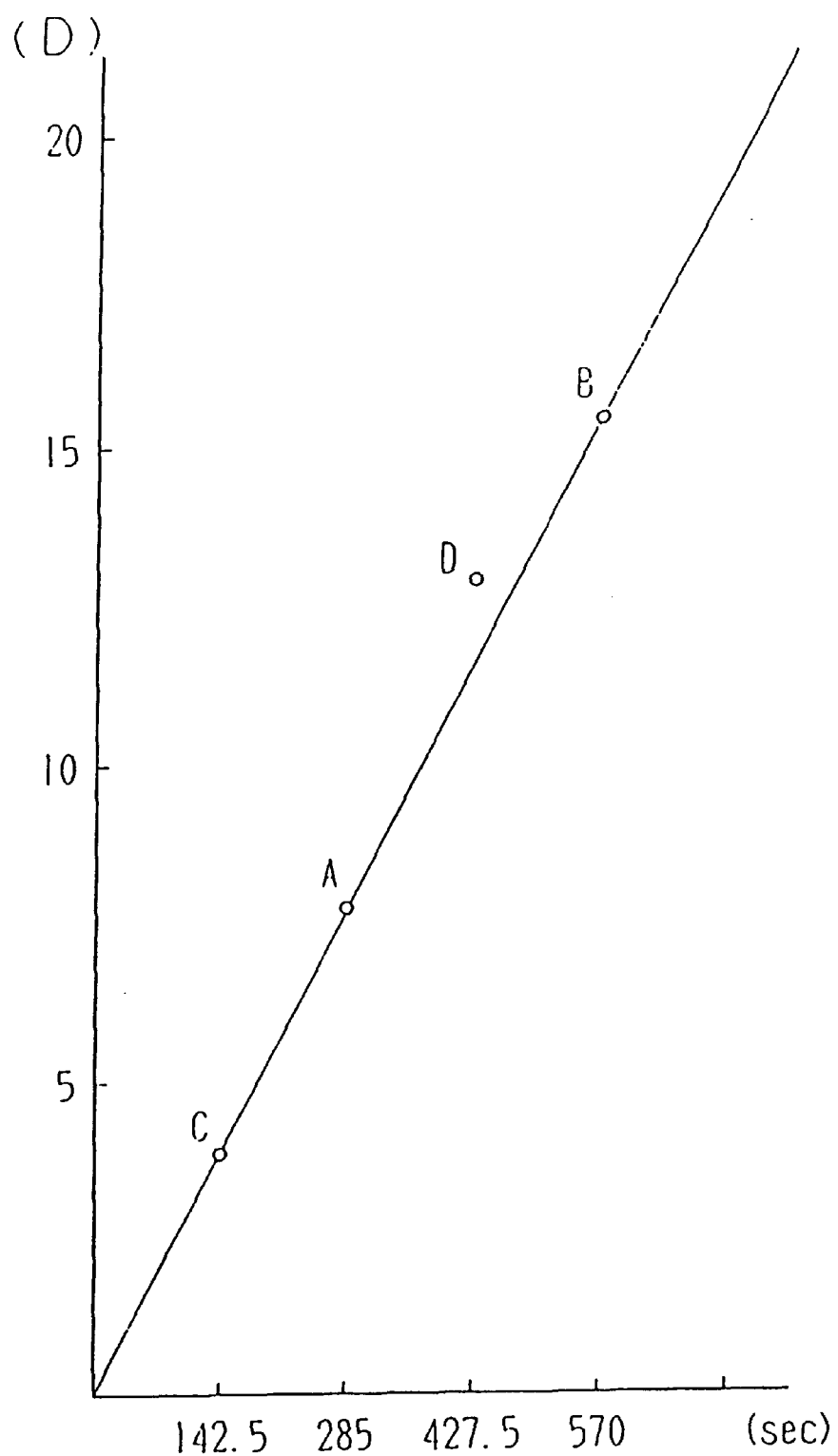
FIG. 12 is a view showing a graph of results of which each power degree of PMMA plate is measured after the ablation by the condition setting in FIG. 11.
Figure 14A:
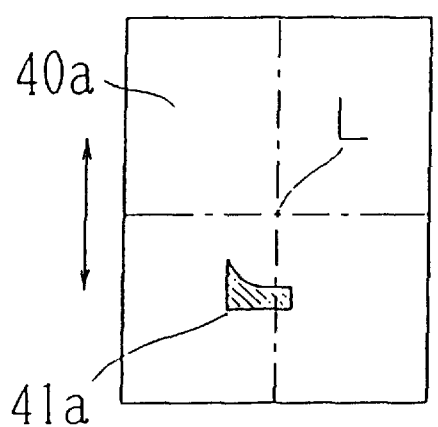
FIGS. 14A–14D are views showing a sample of mask in case that the correction of presbyopia is performed by the ablation for use in the correction of myopia in the apparatus for operating upon a cornea of the present invention.
Figure 14B:
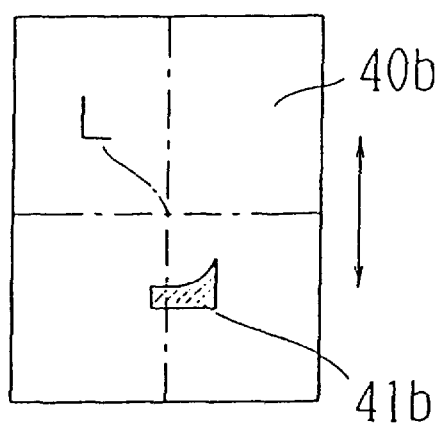
Figure 14C:
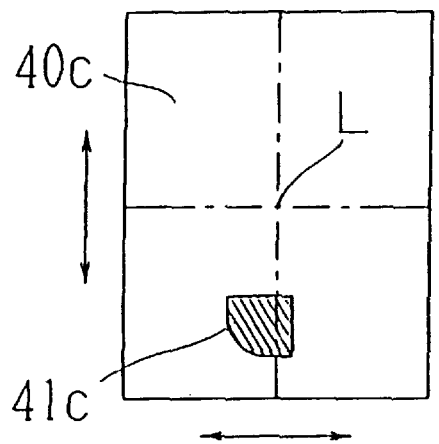
Figure 14D:
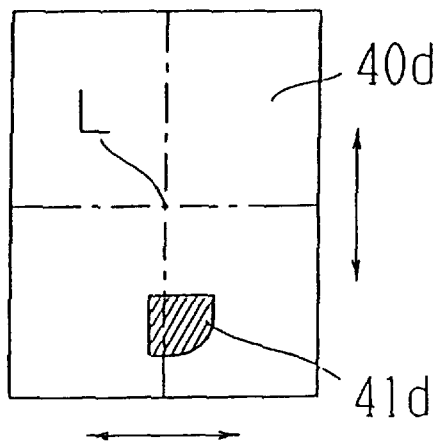

By the combinations of such circular ablation through the above forming process, and by changing the laser beam irradiation time at the shifted position of the beam center, the ablation to be a convex lens shape may be achieved. FIG. 10 is a sample showing one of the combinations. The combination is roughly estimated in order to obtain a refractive power of a certain power based on the depth distribution of sectional shapes as shown in FIGS. 6–9. Without any change of a ratio of the irradiation time at each shifted position as shown in FIG. 10, the PMMA plate is ablated by changing the whole irradiation time under the condition settings A–D as shown in FIG. 11. FIG. 12 is a graph showing results of powers of the PMMA plate after finishing the ablation measured by a lens meter. According to these results, the powers after the ablation may be controlled not by changing the ratio of irradiation pulse-number at each position of laser beam which is shifted from the optical axis L, but by varying the whole irradiation pulse-number.

The above-mentioned controlling of powers may be applied to a cornea that the ablation amount per pulse is equal with the known ration of the PMMA. As a result, tables or operation expressions of power variation for the laser irradiation time (the pulse-number) under a constant irradiation condition is to be stored into the apparatus. On the basis of the above-mentioned conditions, a cornea having a predetermined curvature may be formed (this method is applicable not only to the correction of hypermetropia but also to the correction of myopia).

When the correction of hypermetropia is performed practically, in the apparatus, the movement of the mirror 3, the control of the laser light source 1 and the like are controlled in accordance with a program of the power variation for the whole laser irradiation time based on inputted information by the data input device 21 such as corneal shapes before operation and after operation or the like.

The detailed description related to the above-mentioned method is described in Japanese Laid-open No. 8-66420 corresponding to U.S. patent application Ser. No. 08/466, 430 by the present applicant.

Figure 13A:
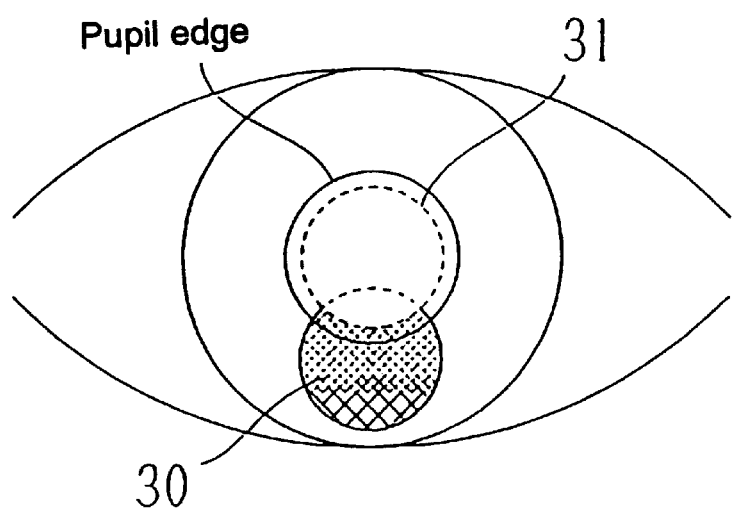
FIGS. 13A and 13B are views explaining the ablation for the correction of presbyopia by the apparatus for operating upon a cornea related to the preferred embodiment of the present invention.

Next, the correction of presbyopia will be described hereinafter. In the method of correcting presbyopia, as shown in FIG. 13A, the ablation is performed so as to increase the refractive power in an oblique-line area 30 adjacent to a pupil edge necessary for the correction of presbyopia, so that the cornea may have double focal points like a presbyopia glasses having an additional lens. That is, by applying the ablation for the correction of hypermetropia at the oblique-line area 30, the correction of presbyopia can be achieved.

The method of ablating the oblique-line area 30 will be described hereinafter. The shifted position of the circular aperture 7 from the optical axis L (in other words, a corneal center or a pupil center) and the aperture diameters are set, and the ablation area is restricted so that the laser beam may be irradiated within the oblique-line area 30. The laser-beam irradiation will be performed as follows. As explained in the stage of the correction of hypermetropia, the beam center is shifted from the optical axis L by the movement of the mirror 3 and is rotated by the image rotator 5, thereby the circular ablation is achieved. When the shifted distance of the beam center is increased, the ablation may be achieved by preventing the center part from being ablated. On the cornea, the laser irradiation is started from the position where a dotted-line area 31 may be avoided from being ablated as shown in FIG. 13A. Then, the ablation is performed by shifting the beam center outwardly in sequence. The control of power is performed in the same process of the correction of hypermetropia that the whole irradiation time (pulse-number) is changed without any change of the ratio of the irradiation time (pulse-number) at each shifted position of the beam center (also, another method may be applicable that the shifting of the beam center may be decreased outwardly). Since it is possible that the ablation amount within the area 31 of the correction of presbyopia may be smaller than of the correction of hypermetropia, the laser irradiation at each shifted position is to be amended against the correction of hypermetropia. Also, it may be desirable that boundary around ablated areas or non-ablated area is to be ablated smoothly. One of the methods is that the aperture diameters of the initialized circular aperture 7 should be enlarged gradually upon the ablation for the correction of presbyopia. By this process, the ablation may be achieved smoothly in up-down and left-right directions.

Figure 13B:
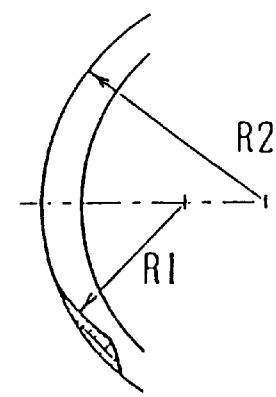

In the process of the correction of presbyopia, the data necessary for information of the ablation area for the correction of presbyopia or the like is inputted by the data input device 21. After an operator fixes a cornea Ec of a patient's eye at a predetermined position, alignment is performed with his observation of the patient's eye by the observation optical system 17. When the alignment is completed, the operator starts operating the apparatus. The controller 20 follows the program for use in the correction of presbyopia based on the inputted data, so that each device; the circular aperture 7, the mirror 3, the image rotator 5, the laser light source 1 or the like are driven and controlled so as to start the laser irradiation. As a result of this process, as shown in FIG. 13B, the oblique-line area 30 may be ablated to be a convex-lens shape so as to achieve the correction of presbyopia.

Figure 15:
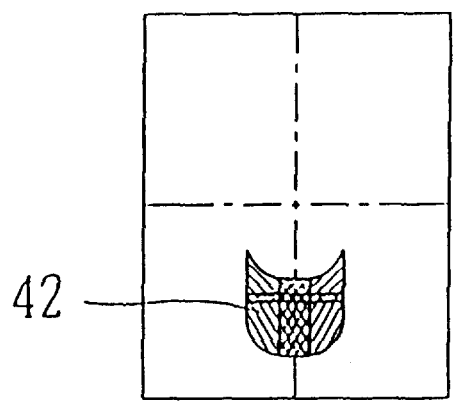
FIG. 15 is a view showing a state when the mask in FIG. 14 is formed on the optical path.
Figure 16A:
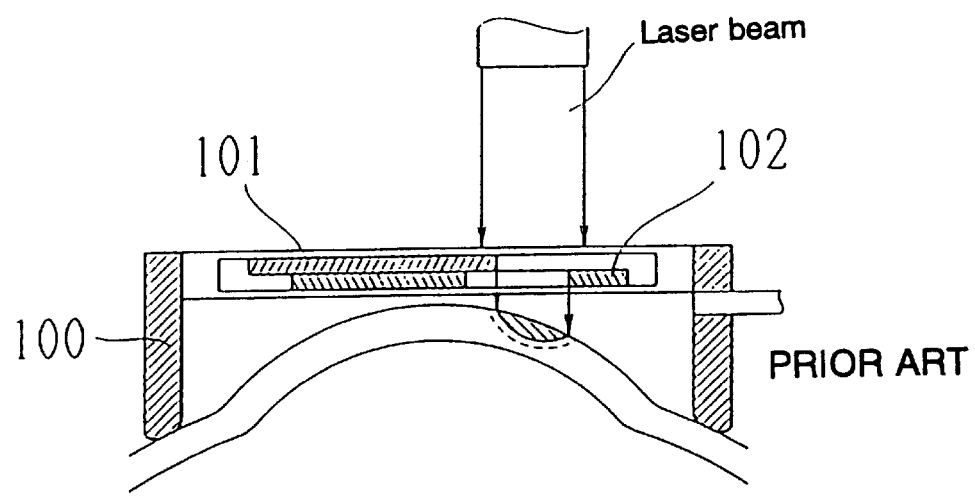
FIGS. 16A and 16B are views explaining the conventional apparatus for the correction of presbyopia.
Figure 16B:
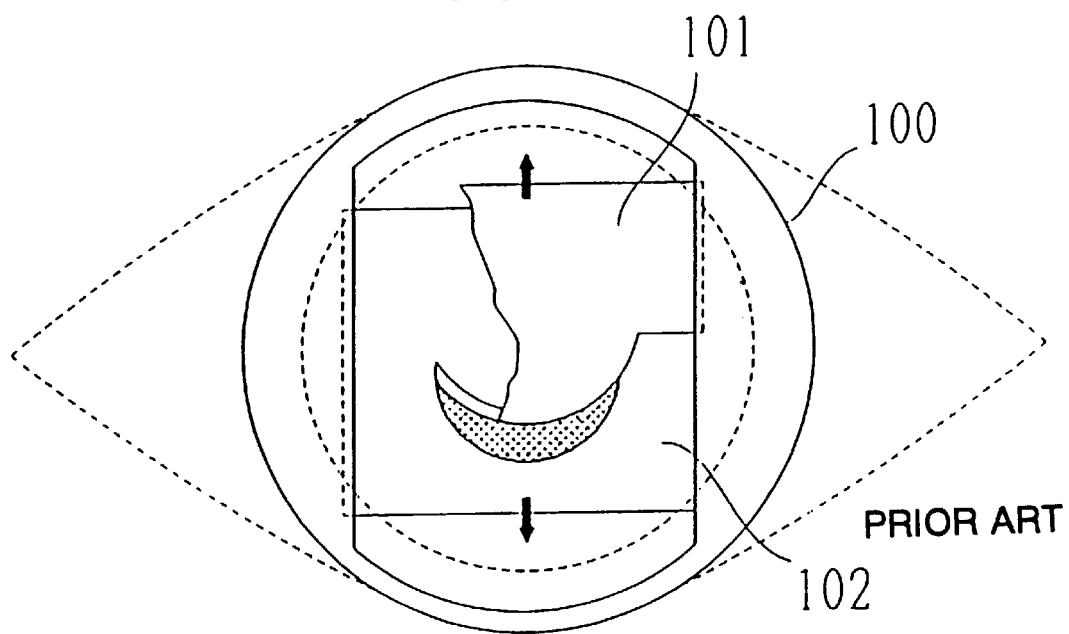

As described above, although the correction of presbyopia is performed by ablating a part of the cornea near the pupil edge necessary for the correction of presbyopia with using the circular aperture 7, in case of performing the correction of presbyopia for an eye with myopia, a part of the cornea may be masked so that the ablation for the correction of myopia is performed around the part. For instance, as shown in FIGS. 14A–D, masking areas 41a–41d that masking parts are divided into four are formed on optical members 40a–40d having characteristic of transmitting the excimer laser beam (wavelength:193 nm). By lapping over the optical members 40a–40d, a mask part 42 is formed on the optical path as shown in FIG. 15 (the mask may be desirable to be located near the circular aperture 7). Also, the optical members 40a–40d are movable by a moving means on the surface which is perpendicular to the optical axis L. The laser beam for use in the above-mentioned correction of myopia is irradiated through the mask. Although the correction of myopia is performed at any other parts except each mask area 41a–41d, the myopia state is remained at the restricted area by the mask 42. As a result of this process, the correction of presbyopia is achieved so that the cornea may have the double focal points. Beside, by driving-controlling that each optical members 40a–40d may be moved gradually with the laser irradiation, the boundary around the ablated part and non-ablated part is formed smoothly.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A system for operating upon a cornea for delivering a laser beam having a wavelength in an ultraviolet range emitted from a laser light source to the cornea, and for correcting ametropia by ablating the cornea with said laser beam, the system comprising:
   a correcting optical subsystem including:
      a moveable aperture which can be positioned so that the center of the moveable aperture can be located at a corneal center when correcting hypermetropia, and which can be positioned so that the center of the moveable aperture is located at a shifted position below the corneal center, such that an opening of said moveable aperture is located at an area including a lower peripheral part of the cornea including an optical part and a non-optical part of the cornea, when correcting presbyopia; and
      a beam-rotator for causing the laser beam shifted from an optical axis of said correcting optical subsystem to rotate about said optical axis;
      wherein said correcting optical subsystem ablates more at the periphery of the cornea than at the center of the cornea when correcting hypermetropia, and said correcting optical subsystem ablates at least the lower peripheral part of the optical part of the cornea as a near-point portion when correcting presbyopia;
   input means for inputting information necessary for defining a corneal shape after ablation;
   determining means for determining the corneal shape based on the information inputted by said input means, and for obtaining an ablation amount of a part of the cornea; and
   controlling means for controlling said laser light source and said correcting optical subsystem;
      wherein said laser light source and said correcting optical subsystem are driven such that said cornea has double focal points upon correction of presbyopia.

2. The system according to claim 1, wherein said correcting optical subsystem further includes beam shifting means for shifting said laser beam opposite to said optical axis.

3. The system according to claim 1, wherein said correcting optical subsystem further includes means for changing a position and size of said aperture.

4. A system for operating upon a cornea for delivering a laser beam having a wavelength in an ultraviolet range emitted from a laser light source to the cornea, and for correcting ametropia by ablating the cornea with said laser beam, the system comprising:
   a correcting optical subsystem including:
      an aperture for myopia correction which restricts an ablation areas, a center of said aperture being located at a corneal center;
      intercepting means which can be positioned at a shifted position below a corneal center and can intercept at least a lower peripheral part of an optical part of the cornea from said laser beam when correcting presbyopia, the intercepting means being capable of changing an intercepted area in size; and
      a beam-rotator for causing the laser beam to rotate about an optical axis of said correcting optical subsystem, wherein said correcting optical subsystem ablates more at the corneal center than at a periphery of the cornea excluding the intercepted area as a near-point portion when correcting myopia and presbyopia;
   input means for inputting information necessary for defining a corneal shape after ablation;
   determining means for determining the corneal shape based on the information inputted by said input means, and for obtaining an ablation amount of a part of the cornea; and
   controlling means for controlling said laser light source and said correcting optical subsystem;

wherein said laser light source and said correcting optical subsystem are driven during correction of myopia and presbyopia such that said cornea has double focal points.

5. The system according to claim 4, wherein said correcting optical subsystem further includes moving means for moving said intercepting means to a desired position.

6. A system for operating upon a cornea comprising:

a laser light source for emitting a laser beam having a beam intensity of Gaussian distribution;

an ablation optical subsystem for correcting ametropia of the cornea by a method of irradiating an eye with the laser beam emitted from said laser light source;

a circular aperture located in said ablation optical subsystem, which restricts an area ablated by said laser beam;

aperture moving means for moving said circular aperture so that a center of the circular aperture may be located at a corneal center when correcting myopia or hypermetropia, and the center of the circular aperture may be located at a shifted position below the corneal center, such that an opening of the circular aperture may be located at an area including a lower peripheral part of the cornea including an optical part and a non-optical part of the cornea, when correcting presbyopia;

beam moving means for moving the laser beam in a direction of Gaussian distribution;

beam rotating means for rotating a moving direction of the laser beam, which is moved by said beam moving means;

information input means for inputting information necessary for defining a corneal shape after ablation;

determining means for determining the corneal shape based on the information inputted by said information input means, and for obtaining an ablation amount of a part of the cornea;

controlling means for controlling said laser light source, said circular aperture, said aperture moving means, said beam moving means and said beam rotating means; and wherein ablation for correcting hypermetropia ablates more at the periphery of the cornea than at the center of the cornea, ablation for correcting myopia ablates more at the center of the cornea than at the periphery of the cornea, and ablation for correcting presbyopia ablates at least the lower peripheral part of the optical part of the cornea as a near-point portion so as to produce double focal points.

7. The system according to claim 6, wherein a diameter of said circular aperture is variable.

8. The system according to claim 1, wherein said correcting optical subsystem ablates the cornea so that an ablation area of the cornea may be loop-shaped when correcting hypermetropia.

9. The system according to claim 6, wherein said correcting optical subsystem ablates the cornea so that an ablation area of the cornea may be loop-shaped when correcting hypermetropia.

10. The system according to claim 1, wherein at least the lower peripheral part of the optical part of the cornea ablated for correcting presbyopia may have more myopic refractive power than another part of the cornea not ablated for correcting presbyopia.

11. The system according to claim 4, wherein said intercepted area of the cornea not ablated for correcting myopia and presbyopia may have more myopic refractive power than another part of the cornea ablated for correcting myopia and presbyopia.

12. The system according to claim 6, wherein at least the lower peripheral part of the optical part of the cornea ablated for correcting presbyopia may have more myopic refractive power than another part of the cornea not ablated for correcting presbyopia.

13. The system according to claim 4, wherein the intercepting means includes quarter-masks which together change the resulting intercepted area of the cornea in shape by overlapping intercepting parts of the quarter-masks.

14. A system for operating on a cornea for delivering a laser beam having a wavelength in an ultraviolet range emitted from a laser light source to the cornea, and for correcting ametropia by ablating the cornea with the laser beam, the system comprising:

an irradiation optical subsystem including:

a laser beam having a boundary extending along a straight line crossing an optical part of the cornea;

boundary shifting means for changing a distance from a corneal center to the laser beam boundary;

beam-rotating means for causing the laser beam to rotate;

an aperture for further limiting the laser beam shaped by the boundary shifting means and rotated by the beam rotating means; and a projecting lens for projecting an image of the aperture on the cornea at a position shifted from the corneal center, said image covering a lower peripheral part of the cornea that includes the optical part of the cornea and a non-optical part of the cornea; and control means for controlling the boundary shifting means and an irradiation amount of the laser beam such that the optical part included in the lower peripheral part of the cornea is made to have a greater refractive power in comparison to another optical part of the cornea.

15. A system for operating upon a cornea, for delivering a laser light beam having a wavelength in an ultraviolet range emitted from a laser light source to the cornea, and for correcting ametropia by ablating the cornea with the laser beam, the system comprising:

an irradiation optical subsystem including an iris diaphragm having an aperture that is variable in diameter and which forms, via a projecting lens, a circular-shaped aperture image upon the cornea that is concentric with respect to the center of the cornea, said laser beam uniformly ablating the circular-shaped aperature image on the cornea;

quarter-masks for intercepting a lower peripheral part of an optical part of the cornea, wherein by overlapping parts of said quarter-masks, an intercepting area formed by said quarter-masks is changed in shape; and control means for ablating the corneal center more than the lower peripheral part of the optical part of the cornea, and for changing the intercepting area formed by said quarter-masks in correspondence with a state of ablation.

* * * * *

UNITED STATES PATENT AND TRADEMARK OFFICE
CERTIFICATE OF CORRECTION

PATENT NO. : 6,190,374 B1
DATED : February 20, 2001
INVENTOR(S) : Masanori AMANO et al.

It is certified that error appears in the above-identified patent and that said Letters Patent is hereby corrected as shown below:

Claim 4, Col. 8, line 45, "areas" should be -- area --.

Claim 12, Col. 10, line 6, "claim 6." should be --claim 6, --.

Claim 15, Col. 10, line 43, after "laser" delete "light beam".

Signed and Sealed this

Fifth Day of June, 2001

*Attest:*

*Attesting Officer*

NICHOLAS P. GODICI
*Acting Director of the United States Patent and Trademark Office*